US005534346A

United States Patent [19]
Robinson

[11] Patent Number: 5,534,346
[45] Date of Patent: Jul. 9, 1996

[54] ATTACHABLE THIN FILM PROPHYLACTIC BARRIER

[76] Inventor: Wilbur D. Robinson, 4571 W. Lake Rd., Canandaigua, N.Y. 14424

[21] Appl. No.: 272,449

[22] Filed: Jul. 11, 1994

Related U.S. Application Data

[63] Continuation of Ser. No. 17,846, Feb. 16, 1993, abandoned.
[51] Int. Cl.$^6$ .................................................. C09J 7/02
[52] U.S. Cl. ........................ 428/343; 428/354; 428/906
[58] Field of Search ................................. 428/343, 354, 428/906

[56] References Cited

U.S. PATENT DOCUMENTS

| | | | |
|---|---|---|---|
| 3,785,102 | 1/1974 | Amos | 52/173 |
| 3,916,447 | 11/1975 | Thompson | 2/46 |
| 3,961,602 | 6/1976 | Dresser | 118/504 |
| 4,107,811 | 8/1978 | Imsande | 15/215 |
| 4,237,223 | 12/1980 | Metz | 428/343 |
| 4,559,671 | 12/1985 | Andrews | 16/111 R |
| 4,722,296 | 2/1988 | Bowskill | 118/504 |
| 5,283,091 | 2/1994 | Darrell et al. | |

FOREIGN PATENT DOCUMENTS

| | | | |
|---|---|---|---|
| 249461 | 12/1987 | European Pat. Off. | 428/343 |
| 3132637 | 3/1983 | Germany | 428/40 |

Primary Examiner—Jenna L. Davis
Attorney, Agent, or Firm—M. Lukacher

[57] ABSTRACT

A disposable, general purpose, protective, prophylactic barrier to aid in preventing cross-contamination from one operation to another. This prophylactic barrier, a visually transparent or translucent, flexible, pliable, planar, rectangular, thin-film, plastic sheet (20), provided with a coating of a low-tack pressure sensitive adhesive over a select adhesive area (22), of its object contacting backside (24), may be bulk packaged for distribution in either a pad (36), or a perforated supply roll (42) format. The sheet (20) may further be printed upon with line indicia, as a guide in identifying work areas essential to the handling and conveying of the sheet (20), with the use of but one hand (52), and also be printed with alphanumeric indicia to delineate instructions for use, advertising, trademarks, and tradenames. The entire physical structure of the prophylactic barrier, in combination, including the sheet (20), a low-tack pressure sensitive adhesive area (22), and printed indicia (34), is most importantly to be generally thin pliable and transparent or translucent so as to enable a user to interact both visually and physically, in a manipulative manner, through the structure of the prophylactic barrier, with any object thereunder positioned.

22 Claims, 4 Drawing Sheets

ATTACHABLE THIN FILM PROPHYLACTIC BARRIER

This is a continuation, of application Ser. No. 08/017,846 filed Feb. 16, 1993 now abandoned.

FIELD OF THE INVENTION

This invention relates to a disposable thin-film prophylactic barrier or sheet, specifically to such sheets which may, even during an operation, be attached in a clean protective manner to any object that might otherwise serve as intermediate host, to carry disease from one operation, and/or patient, to another.

BACKGROUND OF THE INVENTION

Description of Prior Art

In recent years, particularly in consideration of the dangers associated with life threatening infectious diseases and pathogens, such as staphylococcus, HIV/AIDS, Hepatitis B, Salmonella, *E oli* Bacteria, and new strains of Tuberculosis as examples, continuous pressure is mounting to guard against transfer of disease from one person/patient to the next; very notably for example in the dentist's office. The principal object of the present invention is to provide those involved in various operative procedures, say in medicine, surgery, dentistry, laboratories, health care, and food services as examples, a conveniently usable prophylactic barrier or sheet which they may use to prevent the spread of infectious disease from one operation to another.

Nevertheless, various prior art references do pertain to several types of thin, pressure sensitive adhesive coated, sheet type structures, for example, U.S. Pat. No. 3,785,102 Ames, U.S. Pat. No. 4,107,811 Imsande, and U.S. Pat. No. 4,143,194 Wilhkane, all relate to adhesive sheets stacked in pad format for use on floors to collect dust and dirt from objects coming in contact such as shoes, and wheels, etc. It is noteworthy perhaps that each of these structures face the adhesive upward toward the object which may track dirt to the pad's upper surface and are not intended to be placed by hand on individual objects, so as to protectively shield the objects. They are also relatively large in size, for placing in entrance ways to clean rooms. U.S. Pat. No. 3,961,602 Dresser, relates to a peel away self adhering sheet intended to protectively cover butt plates of door hinges to protect them from paint spray or the like, while their associated doors or door frames are being painted. U.S. Pat. No. 3,916,447 Thompson, relates to a soft, flexible, aqueous liquid-barrier web useful as a dinner napkin, bib, furniture cover, or the like. This barrier is intended to cling to soft cloth like materials not to hard objects. U.S. Pat. No. 4,559,671 Andrews, relates to a sterile lamp handle cover to provide a sterile surface for adjustment of a surgical lamp. U.S. Pat. No. 4,237,223 Metz, relates to a test method for determining the presence of microorganisms on a surface. Additionally foreign patent reference 3,132,637 Doring, relates to a continuous film coating with adhesive coating in selected zones to facilitate removal from objects. And foreign patent reference 0,249,461 Riedel, relates to a one pass coating operation method as a process for making tapes for use on mammalian skin. And finally, U.S. Pat. Nos. 4,722,296 and 4,795,669 both to Bowskill relate to a disposable shield for the handle of a light used by dentists or doctors. A new shield is used for each patient, thereby preventing the spreading of contagious diseases. The Bowskill reference falls short of the objectives of the present invention as it does not provide for a user to obtain and use a new shield without touching, and therefore contaminating, the object contacting backside of the shield and the frontside surface of a following shield in the bulk format as well. This being the case it is only possible to use the Bowskill shield prior to, and in preparation for, an operation as opposed to during the operation as can be done with the present invention. Further the Bowskill shield requires that two hands be used in its attachment, it is limited as to the type, shape and orientation of objects which it is intended to protect, it does not provide for tactile and visual feedback for operator interaction with underlying objects, it is aimed at protecting specific objects as opposed to generally protecting a great variety of objects, it requires special receiving hardware with which to be used (a special handle), its reliability to protect against cross contamination is suspect, and it is cumbersome and time consuming to employ when compared to the present invention. Although each of these patents relate to general cleanliness, sanitation and/or sterile related matters, and most are also generally rectangular, thin, and sheetlike and with adhesive elements, all lack at least two significant advantages of the present invention, i.e. they do not provide a structure suitable for protective placement over any object with the use of but one free hand, and they do not provide for a visual and physically manipulative freedom of interaction between the user and the shielded object.

Objects and Advantages

Accordingly, several objects and advantages to the structure of the present invention are as follows:

(a) To provide a general purpose barrier or sheet, easily used, with the use of but one free hand, to protectively isolate a great variety of forms, shapes, and objects which may otherwise serve as intermediate host to carry infectious disease from one operational procedure to another.

(b) To provide the user access to obtaining and controlling a single sheet, from a supply of many sheets, albeit with the use of but one free hand covered with a wet, as in wet with blood, occult blood and body fluids, or a dry latex glove, and a structure that will promote doing this without touching the side of the sheet that is to come in contact with the object there underlying, i.e. to keep the back surface of the sheet, that is to come in contact with the object, free of contaminants.

(c) To provide the user a sheet structure capable of transport to any solid surface, or object regardless of its shape or its orientation, with the use of but the same one wet, or dry, glove covered hand.

(d) To provide the user capability of attaching the single sheet in a manner conforming to the shape of any underlying object, again with the use of but the one same free hand that was used to convey the sheet to the object.

(e) To provide a visually transparent or translucent quality coupled with an ultra-thin pliable structure so as to promote visual and/or physically manipulative interaction between the user and the chosen underlying object, say an instrument control knob, dial, or switch, for example.

(f) To provide a prophylactic, disposable sheet having a clean, sanitary, controllable release, of an attached sheet, from the protected underlying object, again with the use of but one glove protected hand.

(g) To provide a prophylactic sheet with a visual indication on a surface of the sheet which will enable the user to readily distinguish visually between an adhesive backed attachment portion of the sheet and a non-adhesive backed handling portion of the sheet.

(h) To provide a prophylactic sheet with a visual indicia, useful for displaying instructional information, warnings, trade names, trade marks, copyright symbols, and/or advertising information, etc.

(i) To provide a prophylactic sheet for many fields of application such as dental procedures, surgery, hygienists procedures, health care procedures, food service applications, and even home sanitation measures; indeed any use where its inherent capability to prevent the spread of disease would be indicated.

(j) To provide a prophylactic sheet usable in real time, during an operational procedure, as well as preparatory to the procedure, and especially with the use of but one, wet or dry, glove protected hand.

Further objects and advantages will become apparent from a consideration of the ensuing description and drawings.

BRIEF SUMMARY OF THE INVENTION

The present invention provides operative personnel (users) with a thin film prophylactic barrier, hereafter commonly referred to as a sheet, to enable them to, with the use of but one free hand, protectively shield a variety of objects which they might otherwise contaminate, or be contaminated by, during an operational procedure. The sheet has a skirt extending from an area of the sheet having self-adhering tacky material on one side of the sheet over the area. The user can grasp the sheet in this area or by the use of the fingers of one hand. The sheet can be carried by the user from a dispenser to the object to be shielded and released and removed from the object also by grasping the sheet with the fingers of one hand.

Moreover, a thin, pliable, transparent or translucent structure of the sheet will enable the user to both visually and physically interact manipulatively with any shielded object thereunder positioned, regardless of orientation. A further feature of the invention provides indicia to communicate warnings, instructions, identification of handling and non-handling surfaces, tradenames, trademarks, symbols, logos, and/or advertising, etc. Many sheets are to be supplied simultaneously in bulk packaged formats, in a perforated roll and in a pad format, even though other packaging formats such as interfold box, non-perforated roll, etc. might also suffice. Whatever the method of bulk supply, it must be aimed at simplifying the user's need to isolate, and gain control of but one sheet at a time, with use of but one hand, without contaminating either the object contacting backside of the sheet in hand, nor the frontside surface of other remaining sheets which may not be used until a subsequent procedure is encountered.

DETAILED DESCRIPTION

Figure 1:
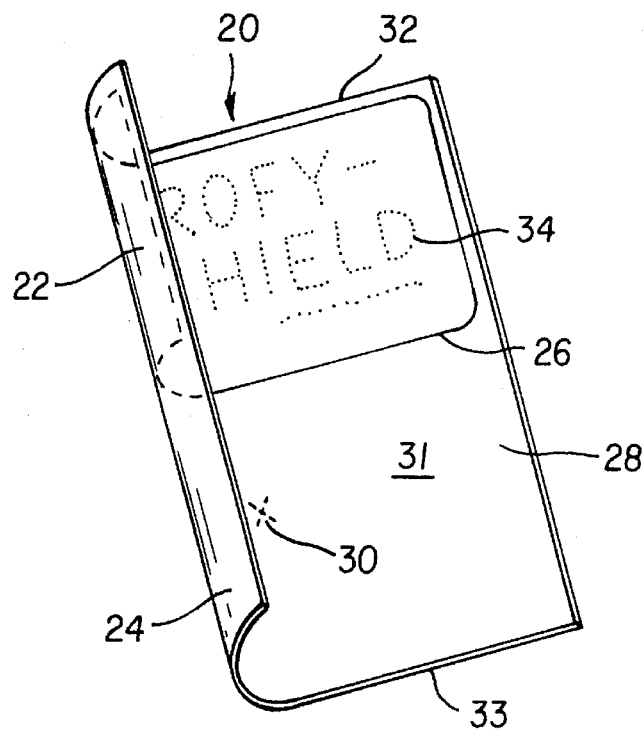
FIG. 1 is a perspective view which shows an embodiment of the invention, namely a singular sheet, configured, not unlike an assembly of several parts, with a specific adhesive area especially allocated for a low-tack pressure sensitive adhesive coating, a specific non-adhesive backed handling area, indicia delineating one area from the other, and other indicia as used to display a trade name for example, all in support of the description of the present invention.

Referring first to FIG. 1, the illustrative embodiment of the present invention comprises a visually transparent, or translucent, flexible, pliable, planar, rectangular, thin-film, plastic, sheet 20, measuring say as but one good example about 0.0005 cm. (0.0002 inches ) thick×20.32 cm. (8 inches) wide×27.31 cm. (10¾ inches) long, but also usable over a wide range of area dimensions as dictated by specific handling and use requirements, and ranging in thickness say from 0.0003 cm. (0.0001 inches) to 0.051 cm. (0.020 inches). The base material of this sheet 20, will most likely be a high density acrylic plastic film, but could also be polyethylene, polypropylene, or other common commercially available thin-film products. In lieu of an exact formulation of this thin material, it is important to note, as one example, of a material that would serve this purpose well, and is believed to be commercially available, is made by the James River Corporation, Food Wrap Business, Parchment, Mich., 49004-1394, and carries the trade name of SATIN PAC, an interfolded clear deli wrap. This James River Product is believed to be FDA Approved, and is very pliable and is translucent. The purpose for preferring transparency or translucency coupled with a very pliable structure is to enable the user to visually and physically interact in a manipulative manner with any object thereunder positioned, say a dial, switch, control, etc.

The aforementioned sheet 20, of the present invention, is further comprised of a very light coating of a low-tack pressure sensitive adhesive, coated only within a strategically select adhesive area 22. This coating should be applied evenly over the select area in a continuous area, or patterned as with dots, squares, lines, diamonds, etc., and the coated select adhesive area 22 should be limited to but a portion of one end of the sheet 20, over, as but an example but not limited to, from not less than 10%, to not more than 75% of the total sheet 20 area, but more generally 33% of the total sheet 20 area, as shown in FIG. 1. Although this light tack-adhesive material itself could be any reasonably effective, releasable, pressure-sensitive, natural or synthetic rubber adhesive, it would best be of an acrylic latex compound suspended in organic solvents as an example, for spray or other means of application directly to the prescribed adhesive area 22, on a reference backside 24, of each sheet 20, preferably so as to maintain at least a visually translucent quality required for a user's visual interaction with underlying objects. Again, as but one example, and in lieu of an exact formulation of this tack adhesive, a commercially available product that would serve the purpose well is made by the Minnesota Mining and Manufacturing Company, 3M Adhesive Systems, Industrial Specialties Division, St. Paul, Minn., 55144-1000, and is sold as 3M SPRAY MOUNT™, ARTIST'S ADHESIVE. Many other commercially available pressure sensitive adhesive compounds can also serve as alternate adhesive materials. It is not the intent of the present invention to delineate process and/or manufacturing methods for either the plastic substrate or the tack adhesive, but rather to prescribe the structural combination and orientation of commercially available materials so as to define a product useful in the field of operations (i.e.—medical, dental, food, etc.) to enable one to prevent cross-contamination between operations.

The exact location of the prescribed coated adhesive area 22 can be identified, as a means of user visual reference, by means of a printed boundary-line indicia 26, as an example. This indicia 26 may be printed on either side of sheet 20: Either on a frontside surface 28, the side which the user will use to handle and position the sheet 20; or on the object contacting backside 24, the side which will ultimately be placed in contact with the intended underlying object. The entire tack-adhesive area 22 could also be identified by an overall coloring or shading, as alternative examples as to how to identify the adhesive area 22 for visual reference in distinguishing it from the non-adhesive backed frontside 28, upon which is located a frontside handling area or skirt 31 which may be puckered and pinched at a pinch point 30. The importance of the limited adhesive area 22, its specific location, and the highlighted means of identifying the adhesive area 22 location cannot be over emphasized, as they all have to do, as will be shown, with the user's ability to obtain but one single sheet 20 from a packaged format of many sheets regardless of the exact nature of the packaging; then to control the sheet 20, convey it, position it, and interact through it, with the use of but one free hand 52 (not shown in FIG. 1) or by puckering the skirt 31 with the fingers while maintaining sanitary conditions on the referenced backside 24; all major objects of the present invention. This is because the adhesive area defines one side of a skirt 31 between an edge thereof and the free edge 33 of the sheet. As shown in the drawings the adhesive area covers about 30–40% of the length of the sheet between the free edge 33 and an edge 32 opposite thereto called the "reference edge."

Experimentation has shown that the adhesive area 22 that best satisfies the needs of the present invention is between 10 and 75 percent, but more generally 33% of the entire object contacting backside 24, of sheet 20, as shown in FIG. 1.

Referenced, and numbered additionally in FIG. 1 are: A short reference edge 32, i.e. the 20.32 cm. (8 inch) dimension as shown; and an example of printed indicia 34, in this case a possible tradename "PROFY-SHIELD" as an example, another might be "SAFE-GUARD", etc. Other useful examples of intended use of surface printing include instructional information, warnings, tradename and/or trademark, logo, copyright symbol, other symbols, advertising information, etc.

Figure 2:
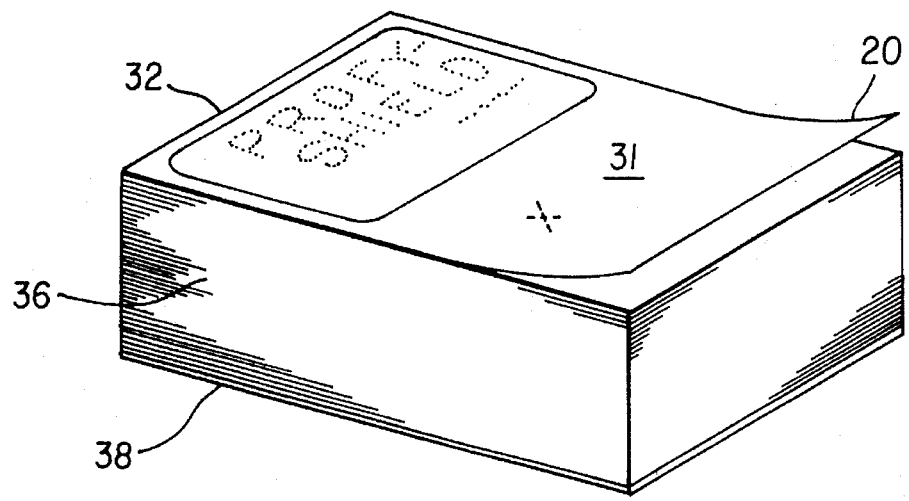
FIG. 2 shows a pad as a bulk supply, or packaging of many sheets of FIG. 1 together for distribution in accordance with the invention..

Best seen in FIG. 2, is a method of supplying many sheets 20, each available with any or all of the same features as were described above for the single sheet 20 shown in FIG. 1, but presented in a very probable pad 36 distribution format, and each being held in place within the pad 36 by the low-tack pressure sensitive adhesive coated strategically within the adhesive area 22, on the object contacting backside 24 of each sheet 20. The pad is then provided a special adhering base card 38 which is to be of a stiffer, more rigid alternative material such as thicker plastic or cardboard, and regardless of the bottom sheet 38 material, it is amply covered over its downward facing surface with a separate pressure sensitive contact adhesive (not numbered), sheltered during the period of distribution by a peel away plastic sheet, whereby the peel away sheet (not shown in FIG. 2) may be removed so as to expose the separate underlying pressure sensitive adhesive, thereby enabling the user to position and secure the pad 36 to any flat surface, such as a desk or table top, so as to expose the first sheet 20 in the pad 36 to ready user access and resist pad 36 movement during sheet 20 removal.

Figure 3:
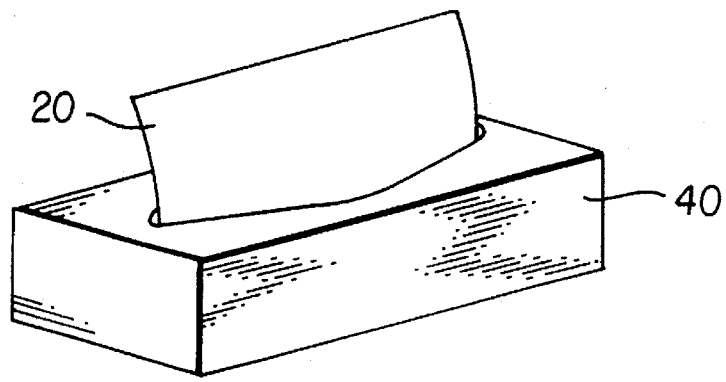
FIG. 3 is a perspective view which shows a box containing interfolded sheets which dispenses the sheets of FIG. 1, in accordance with the invention.

FIG. 3 shows similarly, another possible though less probable method of bulk supply; a sheet dispensing box 40 filled with many interfolded sheets 20, folded in a manner similar to simple tissue supply methods, whereby one leading sheet 20, pulls along a following sheet, each time a sheet is removed from the sheet-dispensing box 40. Again, any and all of the same features as were described earlier for the single sheet 20 shown in FIG. 1, are possible in this supply format as well, with the exception possibly of the tack-adhesive method for attachment.

Figure 4:
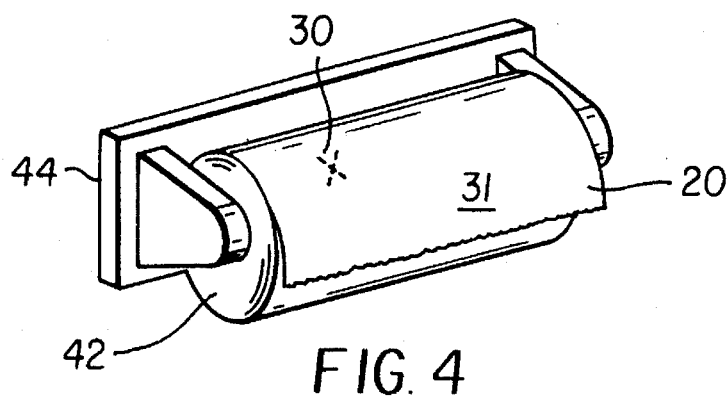
FIG. 4 is a perspective view which shows a roll as containing a succession of sheets, the roll being mounted on an inertially resistive roll holding device.

FIG. 4 shows yet another probable packaging format for supplying many sheets 20 for distribution and use; this time in a perforated roll 42 format, very much the same as common household rolls of paper toweling. FIG. 4 further shows a simple roll holding device 44, again much the same as the simple bracket used to dispense common household paper toweling. In this format, each sheet 20 is separated from the next by a line of tear-away perforations (not yet visible), intended to enable a user to tear free one sheet 20 at a time, from the perforated roll 42, each sheet 20 being available with any or all of the same features described in the previous descriptions of a single sheet as is seen by referring back to FIG. 1.

Figure 5:
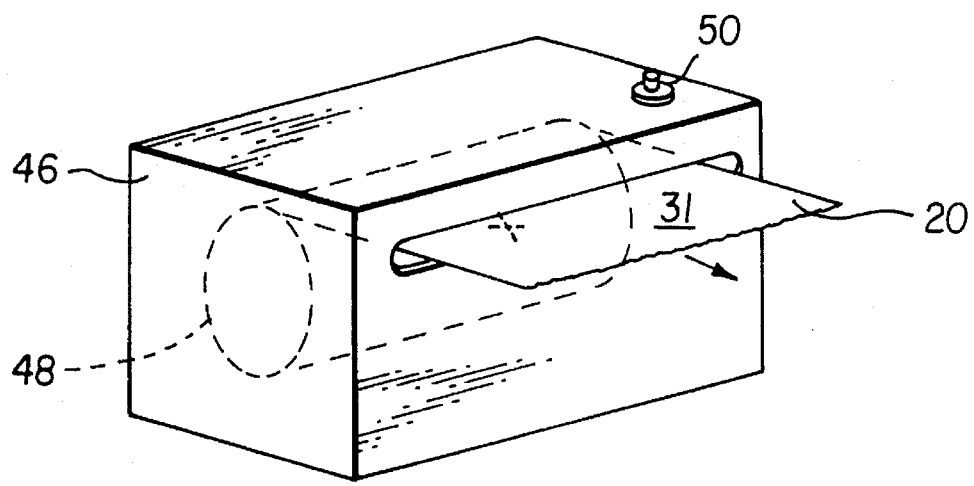
FIG. 5 is a perspective view which shows a more complex dispensing device for automatic cutting and feeding of one sheet according to FIG. 1 at a time, from a continuous non-perforated rolled strip supply format, upon push-button demand.

FIG. 5 depicts conceptually a more complex automatic cutter/feeder 46, a device for automatically cutting and dispensing but a single sheet 20 on demand from a continuous long wound strip, or non-perforated roll 48. It is not the intent of the present invention to delineate all possible bulk packaging formats which might be used to package and distribute the present invention, but rather to show ways by which the sheet 20 might be distributed to better understand how it, the sheet 20, could be used. The important point to be made is that the user must be enabled to isolate, and gain control of but one sheet 20 at a time, with use of but one hand 52 (not shown in FIG. 5), without contaminating either the object contacting backside 24 (FIG. 1) of that sheet 20(FIG. 1), or the frontside surface 28(FIG), of the following sheet 20 which may not be used until a subsequent operation is attempted.

OPERATION—FIGS. 2–11

For the sake of simplicity and brevity, the description of the use of the present invention, will be limited to the assumption that sheet 20 be one being removed from a bulk supply, in a perforated roll format, as can be seen in FIG. 4, and FIGS. 6 to 8. Thus this is one common combination of the embodiment of the present invention, and it further employs the simple roll holding device 44, as the sheet 20 dispensing aid, also shown in FIG. 4. It is henceforth hypothesized that once any sheet 20 is obtained from its packaged supply format, regardless of the exact nature of that packaged format, the method of handling and attaching the sheet 20 to any object thereunder positioned, remains the same in all cases. The manner of obtaining and controlling but one sheet 20, regardless of the exact nature of the supply format, is also held as obvious, by the nature of the supply format, the intent of the user, and the dispensing apparatus, if any.

Figure 6:
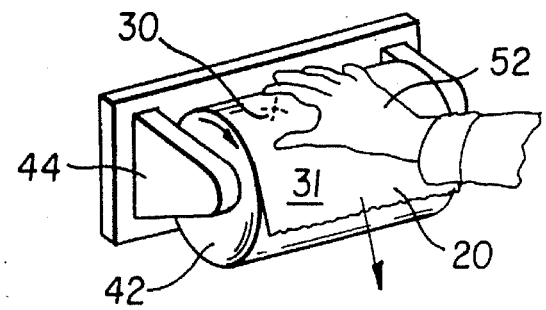
FIG. 6 is a perspective view which shows the device of FIG. 4 with the perforated roll being partially unrolled to provide user access to a graspable, handling portion of the single sheet for subsequent removal of the sheet from the supply roll.

Therefore, referring to FIG. 6, the prescribed manner of obtaining the single sheet 20 from the perforated supply roll 42, is to use one free hand 52 to unroll the perforated roll 42, relative to its roll holding device 44, far enough so as to enable the user to have access to the prescribed frontside handling area or skirt 31 area at pinch point 30, albeit in a position where the pinch point 30, is backed up by the solid nature of the parent perforated supply roll 42.

Figure 7:
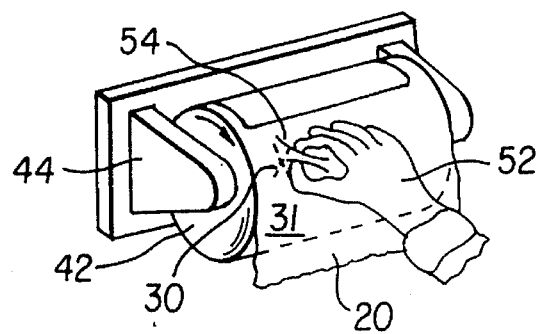
FIG. 7 is another perspective view of the device of FIG. 4 which shows the intended manner of grasping a single sheet, in lead position on a perforated roll, by forming a wrinkle within the allocated grasping and handling area, with the use of but one glove protected free hand.

Referring next to FIG. 7, after obtaining the desired position described above, the user grasps the exposed surface of sheet 20, at the prescribed pinch point 30, between thumb and forefinger of the hand 52 as shown, and using the firm support of the roll 42, forces a wrinkle 54 to form. This formed wrinkle 54 will enable the user to pinch the sheet material between the thumb and forefinger, thereby providing the user the control needed to continue the process of obtaining and conveying the single sheet 20, and most importantly without need to contaminate the referenced backside of sheet 20, or outer surfaces of any subsequently following sheets, yet remaining in the perforated supply roll 42.

Figure 8:
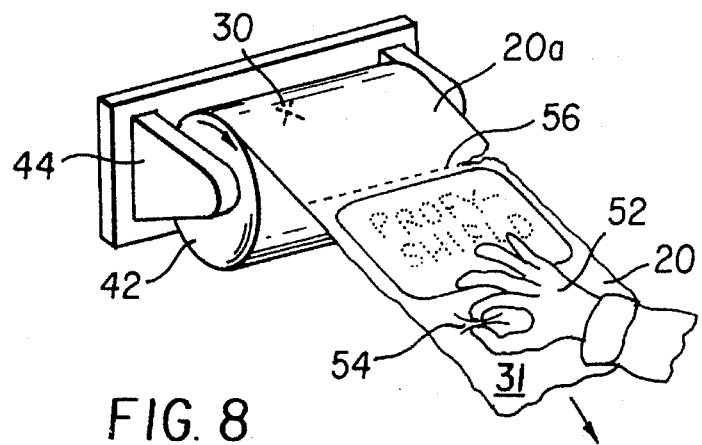
FIG. 8 is a view like FIG. 6 which shows the perforated roll being further unrolled, by the user's pulling on the grasped sheet, to a position revealing a line of tear-away perforations provided to facilitate easy removal, of a single sheet, with use of but the same one hand.

Then, referring to FIG. 8, the perforated supply roll 42, mounted on its roll holding device 44, is further unwound by the user's pulling on the sheet 20, pinched between thumb and forefinger of hand 52, to a position as shown, whereby a line of tear-away perforations 56, separating one sheet 20 from the next sheet 20$_a$, is exposed to view. Then the user tears the single sheet 20 free of the perforated supply roll 42, along the line of tear-away perforations 56, by tearing quickly with an action of the hand 52, wrist, and the free supporting fingers of the hand 52, which have been extended in a fan shape, supportive of sheet 20.

Resistance to an unwanted further unwinding of the perforated roll 42, from its holding device 44, as a result of the tearing away of the single sheet 20, is provided by the rapidity of the tearing effort being opposed by the inertia of the roll 42 itself, and also by the resistive forces which exist at the interface between the roll holding device 44, and the internal surface of the roll 42 supply core (not numbered).

Thus with the sheet 20 now free of its parent perforated roll, and in control of the hand 52, the user is free to transport or convey the single sheet 20 to a position which will shield an object as intended. Explaining this sequence of actions is best begun by orienting the hand 52 and wrist in a manner that the palm faces upward and the sheet 20, being pinched between the thumb and forefinger, rests on the palm and the three remaining extended fingers of hand 52. Once the sheet 20 is established in this horizontal position, held by gravity against the hand 52, it is quite natural to move the hand 52 upward, into the face of still air, in a manner that results in the creation of a relative wind force. This force augments the force of gravity which had by itself previously held the sheet 20 against the outstretched fingers and palm of the hand 52.

Figure 9:
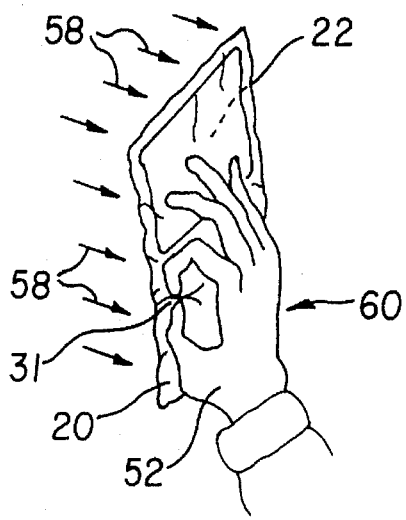
FIG. 9 is a perspective view which shows transporting a single sheet of FIG. 1, making use of the user's spreading of the three free fingers of the hand and by constant movement of the hand through the air, maintaining a force, resulting from the relative wind force created by the movement, which will hold the very light thin film-like sheet against the outstretched fingers.

Referring next to FIG. 9, once this augmenting force has been established, the user is then free to roll his/her hand 52 out of the palm up position, as the relative wind force 58, created by a same continuing hand movement 60 and sheet 20 through the air, will hold the sheet 20 conveniently against the outstretched fingers of the hand 52. This force thus created becomes enough to overcomes gravity's effect on the ultra-light weight sheet 20, enabling the user to continue the conveyance of sheet 20, while maintaining a relatively flat unfolded form to the sheet 20, until the tack-adhesive being confined to adhesive area 22, comes in contact with the object selected by the user to be shielded, as best seen by referring to the next FIG. 10.

Figure 10:
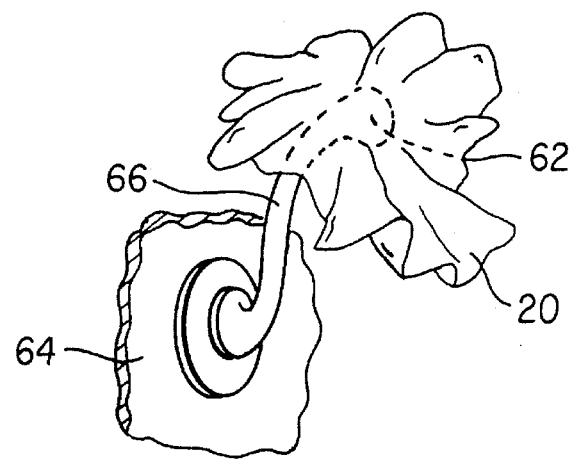
FIG. 10 is a perspective view which shows the single sheet often having been transported to an object to be shielded, and attached to conform to the shape of the object intended to be shielded, in this case a dentist's chair adjustment lever knob.

Referring then to FIG. 10, once the tack-adhesive contacts the selected object, in this case a knob 62, at the end of a dentist's chair 64 adjustment lever 66, it becomes a simple matter for the user to roll the palm or the fingertips of his/her hand 52 so as to conform sheet 20 to the shape of the underlying knob 62, thereby firmly attaching the sheet 20 to the knob 62 in a protectively shielding manner regardless of the objects physical orientation. Because the protective sheet 20 is preferably translucent or transparent, and also pliable in nature, it becomes a simple matter, for the dentist in this example, to visually relate to, and continue any desired physically manipulative interaction with, the adjustment lever 66 knob 62. It is obvious that the same would be true regardless of the exact nature of the underlying object, or what the nature of the operation might be, i.e. medical, dental, health care, food service, etc. on ad infinitum, even as a simple sanitation measure, for example, in covering a home refrigerator handle, or water faucet handle.

Figure 11:
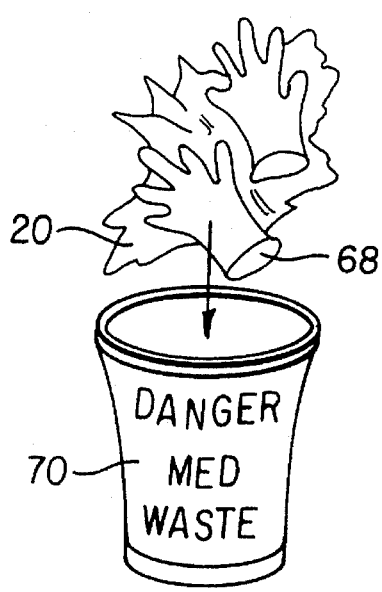
FIG. 11 is a diagrammatic perspective view which shows disposing of several used sheets of FIG. 1, along with used surgical latex gloves, in an appropriate medical waste receptacle.

Finally, referring to FIG. 11, once the given operational procedure is complete, regardless of its nature, any number of used sheets 20 are removed and collected from their respective locations and disposed of appropriately, along with any surgical latex gloves 68 which may have been worn during the operation, in this example into a safe medical waste receptacle 70.

The Disposable Prophylactic Barrier, described as the present invention and commonly called the sheet 20, can be used by operatives, albeit with the use of but one hand only, in many different operational disciplines to protectively in a non-restrictive manner shield a great variety of objects which they might otherwise contaminate during normal operational procedures. These objects can be shielded regardless of their form, shape, or orientation so long as they are solid, and that they may importantly also be shielded real-time during a procedure, as well as before the procedure begins, as certainly a patient would prefer to see. Examples of some of these referred to objects, and their associated disciplines are as follows:

(a) In Dentistry, apparent surface areas of concern are found on the chair adjustment knob, the instrument tray, instrument supply drawer handles, water faucets, examination light adjustment handle, timers, mixers, etc. i.e. anything that the dentist or his assistant may wish to access during the course of the procedure. These items apply equally to dental hygienist operational procedures as to the dentist's procedures.

(b) In the medical doctor's office, there are examination table adjustment surfaces to be concerned about, light switches, cabinet access knobs, chairs, examination lights, etc., i.e. again anything which the doctor, or assisting operative, may need to contact during a given procedure which he/she may have contacted during a previous procedure, or may need to contact again in a subsequent procedure.

(c) In all human surgical operations there are many objects which should be shielded. For example, surgical operation lighting and examination lamps, rails on gurneys, adjustment levers on operation tables, various patient positioning appliances and hardware, control switches and adjustment knobs located on a great variety of life support systems such as dialysis machines, heart lung machines, vital sign monitoring equipment, electrical shock paddles, etc.

(d) In the medical, research, or pathology lab, typical examples of items that should be shielded are microscopes, autoclaves, centrifuges, test tube racks, incubation chambers, etc.

(e) In health care applications such as nursing homes typical examples are bed pans, flushing controls, toilet seats, blood sampling and handling apparatus, health care equipment controls, etc.

(f) In the food service industry, for example in a serving line where a food server wearing food laden latex gloves may have need to adjust warming lamps, or open refrigerator doors, etc. where it would suggest good sanitation practice to not leave deposits of grease or food bits on surfaces to putrefy before subsequent days or weeks serving activities.

(g) Similarly in the residential home kitchen, protecting various surfaces such as sink faucets, refrigerator handles, and dishwasher handles at times when food was being prepared would save the cook wiping food, oils, etc. from his/her hands, say with a paper towel, every time they need to access these items. This use would promote good sanitation, and habits of cleanliness, that many housekeepers strive to maintain.

The advantage that use of these sheets would have over uncertain hit or miss disinfection procedures, that are often only said to be in place but not shown to be, is obvious; i.e. the hapless patient would be able to see the health protective measure in place and be reassured by it.

Although the description above contains many specificities, these should not be construed as limiting the scope of the present invention but as merely providing illustrations of some of the presently preferred embodiments of this invention. For example, the sheets could be made with other shapes such as square, partially oval, clipped diamond or back to back trapezoidal shapes, etc.

What is claimed is:

1. Apparatus for protecting an object prophylactically which comprises a sheet of thin pliable plastic material, sufficiently thin to deform when manually pinched between thumb and forefinger of one hand, and being of the order of from 0.0003 cm. (0.0001 in.) to 0.051 cm. (0.020 in.) thick, and of sufficient area to shield said object of protection when said Sheet is placed upon said object, said area of said sheet further defined as being essentially of uninterrupted rectangular form, said sheet having opposite side edges and first and second opposite end edges, said sheet also having top and bottom opposite surfaces, with said bottom opposite surface alone. having thereon an adhesive material for adhering said sheet to said object, said adhesive material being a releasable material for releasing said sheet when it is pulled away from said object, said adhesive material covering a first area on said bottom surface of said sheet equal in area to about one-half of said area of said sheet, said first area on said bottom surface of said sheet being essentially an adhesive area, said adhesive area extending from adjacent to said first of said opposite end edges toward said second of said opposite end edges and along said opposite side edges of said sheet, a second area between said adhesive area and the extreme outside limit of said second of said opposite end edges defining a nontacky skirt, said nontacky skirt being free of any said adhesive whatsoever, said skirt depending from said adhesive area and defining an area whereupon said top opposite surface of said sheet can be pinched, and grasped with but said one hand, said one hand needing therefore to contact said top surface alone, in order to gain control over said sheet.

2. The apparatus according to claim 1, wherein said sheet is rectangular, said opposite side edges defining the width of said sheet, said opposite end edges defining the length of said sheet, said adhesive area being rectilinear and having end edges and side edges, said end edges of said adhesive area parallelling said end edges of said sheet and one of said end edges of said adhesive area being spaced from said second end edge of said sheet by more than 50% of the length of said sheet thereby defining the area of said skirt which is larger than said adhesive area.

3. The apparatus according to claim 2 wherein said skirt area is rectangular in shape.

4. The apparatus according to claim 1 wherein said sheet has visible indicia thereon demarking the adhesive area and indicating the location of said skirt area.

5. The apparatus according to claim 1 wherein said material of said sheet is a light transmissive plastic.

6. The apparatus according to claim 5 wherein said light transmissive plastic is selected from the group consisting of acrylic, polyethylene, polypropylene, and vinyl.

7. The apparatus according to claim 5 wherein said area of said sheet is of the order of from 7.62 cm. (3 in.) to 25.4 cm. (10 in.) in width, and from 10.16 cm. (4 in.) to 33.02 cm. (13 in.) in length, 8. The apparatus according to claim 1 wherein a plurality of said sheets is arranged in a pad having said adhesive areas of successive ones of said sheets and said areas of said skirts of said successive ones of said sheets disposed in an overlying relationship, whereby said adhesive area faces downward into said pad.

9. The apparatus according to claim 1 wherein a plurality of said sheets are disposed in a box having an opening, and wherein said sheets are further disposed in a successively interfolded relationship with said skirt areas ahead of said adhesive areas in a direction outwardly of said box via said opening, the skirts of successive ones of said sheets extending outwardly of said box through said opening each in turn.

10. The apparatus according to claim 1 wherein a plurality of said sheets are successively wound into a roll with said skirt areas following said adhesive areas of said sheets, whereby said adhesive areas face inward into said roll.

11. The apparatus according to claim 10 which further comprises a holder/dispenser, said holder/dispenser having arms on which said roll may be journalled.

12. The apparatus according to claim 10 wherein successive ones of said sheets are separated by perforations, said perforations being formed as a straight line of said perforations extending from one of said opposite side edges to the other of said opposite side edges, and formed so as to be generally perpendicular to both of said opposite side edges, said straight line of said perforations defining the boundary between said successive ones of said sheets, said boundary being coincidental with said first said opposite end edge and said second said opposite end edge of said successive ones of said sheets.

13. The apparatus according to claim 8 which further comprises a base of rigid material, having upward and downward facing surfaces, said downward facing (outside) surface of said base being covered in its entirety with a releasable contact adhesive for securing said pad to a surface, said releasable contact adhesive in turn being protectively covered with a removable protective covering sheet, said removable protective covering sheet being removable so as to facilitate adhering said base of said pad to said surface.

14. Apparatus for protecting an object prophylactically which comprises a sheet of thin pliable light transmissive plastic material, sufficiently thin to deform when manually pinched between thumb and forefinger of one hand, and of sufficient area to shield said object of protection whenever said sheet is placed upon said object, said area of said sheet further defined as being essentially of uninterrupted rectangular form, said sheet having opposite side edges and first and second opposite end edges, said sheet also having top and bottom opposite surfaces, with said bottom opposite surface alone, having thereon an adhesive material for adhering said sheet to said object, said adhesive material being a releasable material for releasing said sheet when it is pulled away from said object, said adhesive material covering a first area on said bottom surface of said sheet equal in area to about one-half of said area of said sheet, said first area on said bottom surface of said sheet being essentially an adhesive area, said adhesive area extending from adjacent to said first of said opposite end edges toward said second of said opposite end edges and along said opposite side edges of said sheet, a second area between said adhesive area and the extreme outside limit of said second of said opposite end edges defining a nontacky skirt, said nontacky skirt being free of any said adhesive whatsoever, said skirt depending from said adhesive area and defining an area whereupon said top opposite surface of said sheet can be pinched, and grasped with but said one hand, said one hand needing therefore to contact said top surface alone in order to gain control over said sheet.

15. The apparatus according to claim 14 wherein said sheet may have visible indicia thereon demarcating said adhesive area or said area of said skirt, or both said adhesive area and said area of said skirt.

16. The apparatus according to claim 14 wherein said plastic is selected from the group consisting of acrylic, polyethylene, polypropylene, and vinyl.

17. The apparatus according to claim 14 wherein the thickness of said sheet, being sufficiently thin to deform when pinched, is of the order of from 0.0003 cm. (0.0001 in.) to 0.051 cm. (0.020 in.) and wherein the area of said sheet is defined as measuring of the order of from 7.62 cm. (3 in.) to 25.4 cm. (10 in.) in width, and from 10.16 cm. (4 in.) to 33.02 cm. (13 in.) in length, with exact linear dimensions dictated by application requirements, nevertheless served well in the majority of applications with dimensions of the order of 0.0005 cm. (0.0002 in.) in thickness, 20.32 cm. (8 in.) in width, and 26.67 cm. (10.5 in.) in length.

18. The apparatus according to claim 14 wherein a plurality of said sheets is arranged in a pad having said adhesive areas of successive ones of said sheets and said areas of said skirts of said successive ones of said sheets disposed in an overlying relationship, whereby said adhesive area faces downward into said pad.

19. The apparatus according to claim 14 wherein a plurality of said sheets are disposed in a box having an opening, and wherein said sheets are further disposed in a successively interfolded relationship with said skirt areas ahead of said adhesive areas in a direction outwardly of said box via said opening, the skirts of successive ones of said sheets extending outwardly of said box through said opening each in turn.

20. The apparatus according to claim 14 wherein a plurality of said sheets are successively wound into a roll with said skirt areas following said adhesive areas of said sheets, whereby said adhesive areas face inward into said roll.

21. The apparatus according to claim 14 wherein successive ones of said sheets are separated by perforations, said perforations being formed as a straight line of said perforations extending from one of said opposite side edges to the other of said opposite side edges, and formed so as to be perpendicular to both of said opposite side edges, said straight line of said perforations defining the boundary between said successive ones of said sheets, said boundary being coincidental with said first said opposite end edge and said second said opposite end edge of said successive ones of said sheets.

22. The apparatus according to claim 8 which further comprises a base of rigid material, having upward and downward facing surfaces, said downward facing (outside) surface of said base being covered in its entirety with a releasable contact adhesive for securing said pad to a surface, said releasable contact adhesive in turn being protectively covered with a removable protective covering sheet, said removable protective covering sheet being removable so as to facilitate adhering said base of said pad to said surface.

* * * * *